(12) United States Patent
Schuurmann

(10) Patent No.: US 11,179,201 B2
(45) Date of Patent: Nov. 23, 2021

(54) METHOD FOR DETERMINING A PARAMETER WHICH IS INDICATIVE FOR THE POSITION AND APPOSITION OF A TUBULAR MEMBER, SUCH AS A STENT GRAFT, INSERTED IN A LUMEN OF AN ANATOMICAL VESSEL OR DUCT OF A PATIENT

(71) Applicant: Endovascular Diagnostics B.V., Nieuwegein (NL)

(72) Inventor: Richte Schuurmann, Utrecht (NL)

(73) Assignee: ENDOVASCULAR DIAGNOSTICS B.V., Nieuwegein (NL)

( * ) Notice: Subject to any disclaimer, the term of this patent is extended or adjusted under 35 U.S.C. 154(b) by 256 days.

(21) Appl. No.: 16/302,182

(22) PCT Filed: May 18, 2017

(86) PCT No.: PCT/EP2017/062006
§ 371 (c)(1),
(2) Date: Nov. 16, 2018

(87) PCT Pub. No.: WO2017/198778
PCT Pub. Date: Nov. 23, 2017

(65) Prior Publication Data
US 2019/0209243 A1 Jul. 11, 2019

(30) Foreign Application Priority Data
May 18, 2016 (NL) ..................................... 2016792

(51) Int. Cl.
*G06K 9/00* (2006.01)
*A61B 34/10* (2016.01)
(Continued)

(52) U.S. Cl.
CPC ............ *A61B 34/10* (2016.02); *A61B 5/7275* (2013.01); *A61F 2/07* (2013.01); *G06F 30/20* (2020.01);
(Continued)

(58) Field of Classification Search
CPC ...................................................... A61B 34/10
See application file for complete search history.

(56) References Cited

U.S. PATENT DOCUMENTS

2003/0200120 A1 10/2003 Binkert
2013/0058555 A1* 3/2013 Miao .................. G06K 9/00214
382/132

(Continued)

FOREIGN PATENT DOCUMENTS

| JP | 2001079097 A | 3/2001 |
|----|--------------|--------|
| WO | 2016001278 A1 | 1/2013 |
| WO | 2015121674 A1 | 8/2015 |

OTHER PUBLICATIONS

International Search Report and Written Opinion from PCT/EP2017/062006 dated Jul. 14, 2017, pp. 11.

*Primary Examiner* — Oneal R Mistry
(74) *Attorney, Agent, or Firm* — Kacvinsky Daisak Bluni PLLC

(57) ABSTRACT

A method for determining an apposition parameter indicative for the position and apposition of a tubular member, such as a stent graft, inserted in a lumen of an anatomical vessel/duct of a patient. The method includes providing a numerical three-dimensional patient model of at least a part of the vessel including the tubular member; determining a vessel morphology parameter from the patient model, the parameter indicative for the anatomy of a predetermined part of the vessel at or near the tubular member in said vessel with respect to said patient model; determining a tubular member positional parameter from the patient model, the parameter indicative for the position of a predetermined part of the tubular member in the patient model; and calculating, (Continued)

based on the determined vessel morphology parameter and tubular member positional parameter, the relative position of the tubular member with respect to the vessel as the apposition parameter.

20 Claims, 6 Drawing Sheets

(51) Int. Cl.
*G16H 30/40* (2018.01)
*G16H 50/50* (2018.01)
*G06F 30/20* (2020.01)
*A61B 5/00* (2006.01)
*A61F 2/07* (2013.01)
*G06F 111/10* (2020.01)

(52) U.S. Cl.
CPC ............ *G16H 30/40* (2018.01); *G16H 50/50* (2018.01); *A61B 2034/105* (2016.02); *A61F 2250/0096* (2013.01); *G06F 2111/10* (2020.01)

(56) References Cited

U.S. PATENT DOCUMENTS

| | | | |
|---|---|---|---|
| 2014/0111541 A1* | 4/2014 | Tolkowsky | A61M 25/09 345/632 |
| 2014/0350350 A1 | 11/2014 | Imagawa et al. | |
| 2015/0356734 A1* | 12/2015 | Ooga | A61B 6/5217 382/131 |
| 2016/0232667 A1* | 8/2016 | Taylor | G06K 9/6298 |
| 2016/0247279 A1* | 8/2016 | Lavi | A61B 6/507 |

* cited by examiner

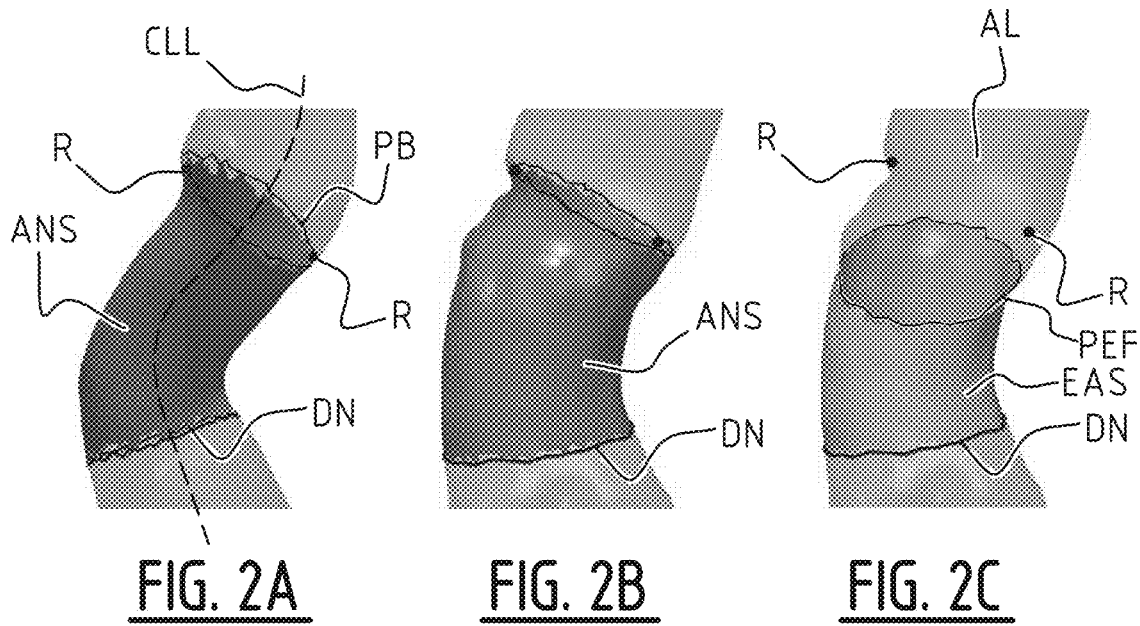
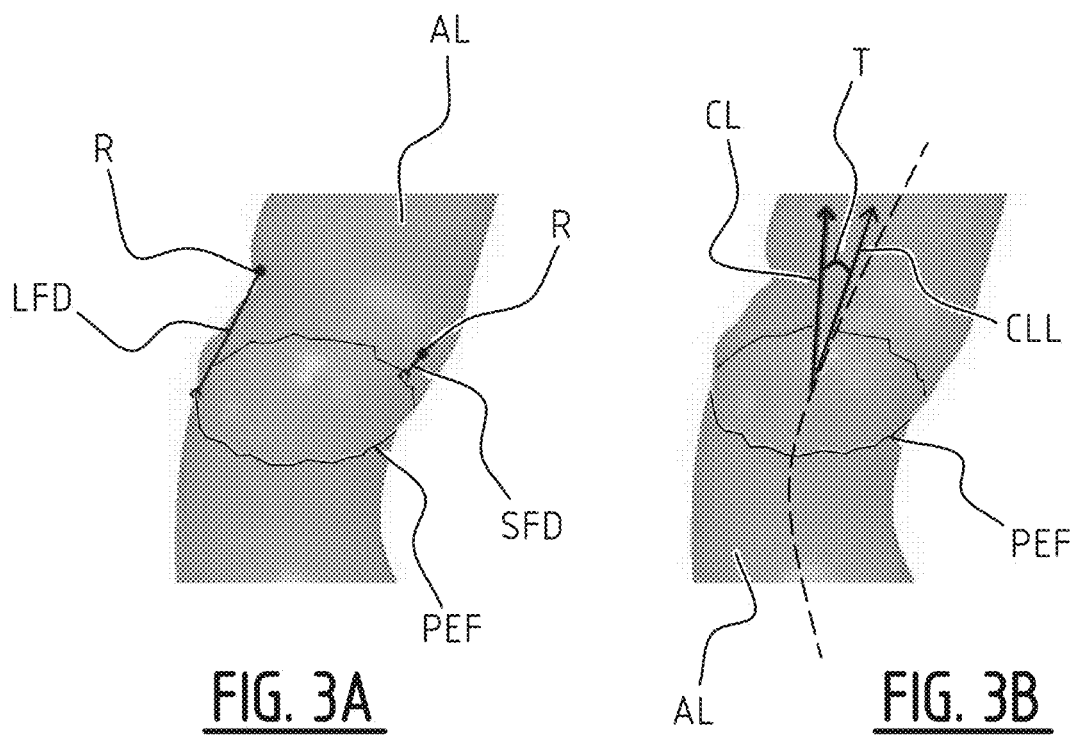

METHOD FOR DETERMINING A PARAMETER WHICH IS INDICATIVE FOR THE POSITION AND APPOSITION OF A TUBULAR MEMBER, SUCH AS A STENT GRAFT, INSERTED IN A LUMEN OF AN ANATOMICAL VESSEL OR DUCT OF A PATIENT

This is a national stage application filed under 35 U.S.C. § 371 of pending international application PCT/EP2017/062006 filed May 18, 2017, which claims priority to Netherlands Patent application NL 2016792, filed May 18, 2016, the entirety of which applications are hereby incorporated by reference herein.

The present invention relates to a method for determining an apposition parameter which is indicative for the position and apposition of a tubular member, such as a stent graft, inserted in a lumen of an anatomical vessel or duct of a patient. The invention further relates to a method for determining an apposition parameter which is indicative for the position and apposition of a stent graft in the thoracoabdominal aorta and iliac arteries of a patient after (thoracic) endovascular aneurysm repair.

Endovascular Aneurysm Repair (EVAR) is the preferred treatment modality for infrarenal abdominal aortic aneurysms (AAA). With the development of latest generation endografts, a trend is seen in treating more complex aortic anatomy. The most limiting factor for EVAR is sufficient sealing in the aortic neck, the area between the lowest renal artery and the aneurysm sac. Short neck length (<10 mm), large aortic neck diameter (>28 mm), large average aortic neck curvature (>21 m$^{-1}$), mural neck calcification)(>10°) and mural neck thrombus)(>23°) have been associated with acute or long-term neck complications, like type IA endoleak and endograft migration. Accurate prediction of the risk for sealing failure is vital for the choice of endograft type and size, in order to minimize the risk for undersizing or misdeployment of the endograft. The same is true for thoracic endovascular aneurysm repair (TEVAR) were full apposition of the stent graft is essential to prevent migration and type IA endoleaks.

Reporting standards describe the aortic neck by neck length and diameter, therefore assuming a cylindrical simplification of the aortic neck morphology. Furthermore, during preoperative planning, position of the endograft perpendicular to the centerline just below the branch artery orifice is assumed. In more complex aortic neck morphology, this assumption may not suffice and may result in increased risk for sealing failure. Complex neck morphology and large thrombus load in the aortic neck may result in undersizing or excessive oversizing of the endograft. Aortic neck curvature and tilt of the endograft may result in loss of apposition surface.

Current (T)EVAR follow-up mainly involves examination of the prevalence of endoleaks and change in maximum aneurysm sac diameter.

It is a goal of the present invention, next to other goals, to provide an efficient, reliable and/or improved method for determining the position and/or apposition of a tubular member, such as a stent graft, in a vessel, such as the thoracoabdominal aorta and iliac arteries.

This goal, amongst other goals, is met by a method according to appended claim 1. More specifically, this goal, amongst other goals, is met by a method for determining an apposition parameter which is indicative for the position and/or apposition of a tubular member, such as a stent graft, inserted in a lumen of an anatomical vessel or duct of a patient, wherein the method comprises the steps of:
  providing a numerical three-dimensional patient model of at least a part of the vessel of the patient including the tubular member;
  determining at least one vessel morphology parameter from the patient model, which parameter is indicative for the anatomy of a predetermined part of the vessel at or near the tubular member in said vessel with respect to said patient model;
  determining at least one tubular member positional parameter from the patient model, which parameter is indicative for the position of a predetermined part of the tubular member in the patient model;
  calculating, on the basis of the determined vessel morphology parameter and tubular member positional parameter, the relative position of the tubular member with respect to the vessel as the apposition parameter.

In contrast to the known follow-up method where the position of the tubular member was visually checked during medical imaging, the method of the invention allows a quantitative determination of the relative position of the tubular member and the vessel based on a three-dimensional, preferably digital, patient model of the patient. The apposition parameter, which may be considered as a measure for the quality of placement of the tubular member in the vessel, is thus preferably a quantitative measure which allows a user, for instance a practitioner, to determine whether a tubular member is correctly located in the vessel. The method preferably comprises the step of outputting the apposition parameter, next to preferably the other determined parameter, to a suitable output, such as a computer screen.

According to a preferred embodiment, the step of determining the vessel morphology parameter comprises determining at least one of the diameter, length and surface of the vessel suitable for receiving said tubular member. This for instance allows checking whether the tubular member as inserted in the vessel covers the area which is suitable for receipt of said tube.

According to a further preferred embodiment, the vessel morphology parameter and the tubular member positional parameter define the anatomy, respectively position in the same three-dimensional coordinate system of the patient model. This allows an efficient determination of the parameters.

In a further preferred embodiment of the method according to the invention, the steps of:
  determining the vessel morphology parameter comprises determining at least one of the proximal and distal boundary in said vessel suitable for receiving the tubular member;
  determining the tubular member positional parameter comprises determining the position of the proximal, respectively distal end of the tubular member in said vessel, and;
  calculating the apposition parameter comprises calculating a ratio or distance between the vessel morphology parameter and the tubular member positional parameter.

A ratio, or any other parameter based on the two previously defined parameters, between for instance the proximal end of the tube and the proximal boundary of the vessel which is still capable of receiving said tube is a measure of correct placement. In case the proximal end and the proximal boundary substantially overlap, it can be assumed that the position of the tube is correct. A distance between the distal parts of the surface and the tube may be an indication that the tubular member is placed to distal with respect to the proximal boundary.

At the same time, a distance between the proximal end of the tubular member and the distal boundary in said vessel is an indication of the contact length or apposition length of the tubular member in the vessel. Also this forms a good measure. This will be explained in greater detail below for the aorta. It will however be appreciated that this, and any other parameters as discussed later on, can be applied to other vessels or ducts within the human or animal body.

Preferably, the step of determining the proximal and/or distal boundary in said vessel comprises identifying in said patient model branch vessels, for instance branch arteries, of said vessel. Vessels branching from the vessel into which the tube is inserted are typically to remain uncovered. By identifying the openings of said branch vessel in said branch, a proximal or distal boundary can be determined.

The part of the vessel suitable to receive a tubular member may further be delimited by an aneurysm. The step of determining the proximal and/or distal boundary in said vessel then preferably comprises identifying the boundary of the aneurysm in said patient model, for instance by identifying a predetermined increase in vessel diameter, for instance with respect to an earlier defined diameter. An increase in for instance 10% of vessel diameter is preferably determined as the boundary of the aneurysm, thereby forming the proximal or distal boundary of the vessel suitable for receiving the tubular member. In most cases for treating an aneurysm, the aneurysm defines the distal boundary of the vessel suitable for receiving the tubular member, wherein the proximal boundary is determined by any branch vessels.

In a further preferred embodiment of the method according to the invention, the steps of:
  determining the vessel morphology parameter comprises determining a center lumen line extending to the cross sectional centers of the lumen along a predetermined length of the vessel;
  determining the tubular member positional parameter comprises determining at least one of a proximal and distal end of the tubular member in said vessel and determining the center line normal to said end surface;
  calculating the apposition parameter comprises calculating the angle between the center lumen line and the center line normal to said end surface.

A discrepancy between the orientation, seen in the three-dimensional space of the patient model, between the proximal end of the tubular member and the local center line in the vessel indicates that the tubular member is misaligned in the vessel.

In order to reliably establish whether the tubular member apposes the lumen of the vessel, in particular the surface of the vessel which is capable and suitable for receiving the tubular member, as desired, it is preferred to calculated the possible, theoretical, apposition surface within the vessel and compare this surface to the outer surface of the tubular member. Therefore, in a further preferred embodiment of the method according to the invention, the steps of:
  determining the vessel morphology parameter comprises determining an inner surface of the lumen of said vessel suitable for receiving the tubular member;
  determining the tubular member positional parameter comprises determining the surface of the tubular member in contact with said inner surface of said lumen;
  calculating the apposition parameter comprises calculating a ratio between the vessel morphology parameter and the tubular member positional parameter.

The surfaces may for instance be determined on the basis of the defined distal and proximal boundaries as explained above. These boundaries may then be compared to the determined actual ends of the tubular member.

A reliable parameter can be established when the progress within a patient is monitored over time. A further preferred embodiment of the method according to the invention thus comprises:
  providing a first numerical three-dimensional patient model obtained from a patient at a first point of time and determining at least one of the parameters from said first patient model;
  providing a second numerical three-dimensional patient model obtained from said patient at a second point of time different from said first point of time and determining at least one of the parameters from said second patient model;
  calculating the apposition parameter on the basis of the parameters determined from the two numerical three-dimensional patient models.

It should be noted that in particular when using different patient models, although also when determining a parameter based on a single patient model as described above, it is possible that the method only includes determining one of the vessel morphology parameter or the tubular member positional parameter. The apposition parameter can then be established based on this single parameter. In particular when comparing these parameters for different patient models, representative for the patient over different points of time, a reliable apposition parameter which is representative for the position and/or apposition, in particular the quality thereof, can be determined.

In order to compare the situation in the patient with the inserted tubular member with the pre-operative situation, the method hereby preferably further comprises the step of providing a numerical three-dimensional pre-operative patient model of at least a part of the vessel of the patient not including the tubular member obtained prior to insertion of the tubular member and calculating at least one of the parameters from said pre-operative patient model. The parameters as calculated from the pre-operative model can for instance be regarded as a base-line for further comparison of the parameters post-operative. As mentioned above, it is then possible that only vessel morphology parameters of two different models in time determine the apposition parameter.

For instance in the case of determining the position of a stent graft in the aorta of a patient after endovascular aneurysm repair, a change in aortic neck morphology, for instance in terms of neck diameter, length or surface, itself may already be indicative of the position and apposition of the stent graft in the neck.

According to a further preferred embodiment, the step of providing a numerical three-dimensional patient model comprises obtaining a three-dimensional image data from a medical imaging technique, such as Computed Tomography (CT), Computed Tomography Angiography (CTA), Magnetic Resonance Imaging (MRI), Magnetic Resonance Angiography (MRA), and the like, and preferably subsequently processing said image data for obtaining said numerical three-dimensional patient model. Providing a three-dimensional model from imaging data as such is known and can for instance be obtained from the medical scanners and associated software.

Preferably, the three-dimensional model comprises three-dimensional positional data of the morphology of the vessel and (in case of the post-operative models), positional data of the tubular member in the vessel. Preferably, the positional data is in the form of a mesh containing coordinates of a plurality of imaging points. As an example, the 3mensio vascular workstation (Pie Medical Imaging BV, Maastricht, The Netherlands) can be used to generate a mesh and subsequent calculations on the patient model such as to obtain center luminal line (CLL) coordinates, a mesh of the lumen of the vessel and coordinates of the boundaries in the vessel, for instance the highest and lowest renal artery origins as will be explained below for the abdominal aorta and distal end of the infrarenal aortic neck, and the proximal end of the tubular member.

As said, current (T)EVAR follow-up mainly involves examination of the prevalence of endoleaks and change in maximum aneurysm sac diameter. However, suboptimal stent graft position and change in neck morphology during follow-up may forecast short or long-term complications. This invention thus provides a method for quantification and visualization of stent graft position and apposition in the aortic neck. The invention thus further relates to a method for determining an apposition parameter which is indicative for the position and apposition of a stent graft in the thoracoabdominal aorta and/or iliac artery of a patient after endovascular aneurysm repair according to the invention.

Preferably, the step of determining the vessel morphology parameter comprises determining at least one of the diameter, length and surface of the aortic neck in said patient model. The neck is described by neck length, neck diameter and neck surface. These characteristics provide a context for the position and apposition of the endograft in the aortic neck. Quantification and possibly visualization, of the neck morphology aids in the interpretation of these variables, since the neck is often of complex morphology.

In order to efficiently calculate the vessel morphology parameters as for instance mentioned above, it is preferred if the distal and proximal boundaries or ends of the vessel, in this case aortic neck, of area which is suitable to receive the tubular member is determined. Preferably the parameters are determined automatically, for instance in a computer implemented method using imaging techniques. As an alternative, the parameters can also be determined (semi) manually.

It is preferred if the step of determining the vessel morphology parameter comprises identifying the positions in the patient model of branch arteries, for instance the renal arteries, and determining the proximal boundary in said vessel suitable for receiving the tubular member as the position in the patient model on the basis of the positions of the branch arteries. As the branch arteries are to preferably to remain uncovered, i.e. preserved, these openings in the aorta define the proximal boundary suitable for receiving the tubular member in the form of a stent.

To determine the distal boundary of the aortic neck, the method preferably comprises the step of determining the vessel morphology parameter comprises determining the distal boundary of the aortic neck, wherein determining the distal boundary comprises:
   in the patient model, which is a post-operative model, determining the first slice or section perpendicular to the center lumen line of the aortic neck that shows interruption of full circumferential stent graft apposition; and/or
   in a pre-operative patient model as mentioned above, determining the first slice or section to exceed a 10% increase of the average aortic diameter at baseline.

The neck diameter is preferably defined as the average of two orthogonal diameters, as preferably measured from adventitia to adventitia at the level of the distal end of the orifice of the lowest branch artery that has to be preserved (baseline).

The length and surface of the aortic neck are then preferably determined on the basis of the determined proximal and distal boundaries of the aortic neck. Specifically, the neck length is preferably defined as the center lumen line (CLL) length from the baseline level of the lowest branch artery to the first slice or section perpendicular to the CLL where the average aortic diameter increases 10% as compared to the baseline level on preoperative patient model or CTA scans if available. On a postoperative patient model or CTA scans, the distal end of the aortic neck is preferably defined by the first slice perpendicular to the CLL that shows interruption of full circumferential stent graft apposition.

Aortic Neck surface (ANS) is preferably defined as the part of the aorta that can optimally be used for stent graft apposition without overstenting an important branch artery. This surface area preferably has a proximal boundary through the origin(s) of branch arteries to be preserved and a distal boundary at the distal end of the aortic neck. In a preoperative patient model or CTA scans, the distal end of the aortic neck is defined as the first slice to exceed a 10% increase of the average aortic diameter at baseline. In a postoperative patient model or CTA scans, the distal end of the aortic neck is defined by the first slice or section perpendicular to the CLL that shows interruption of full circumferential stent graft apposition. The neck surface is calculated from the preoperative CTA scan and the postoperative CTA scans, and preferably the increase or decrease of the surface is calculated ($ANS_{post}/ANS_{pre}*100\%$). The apposition parameter can then be determined as ratio or change in determined vessel morphology parameters for the different patient models as mentioned above, even without determining any tubular member positional parameter.

An increase in neck surface on the first postoperative CTA scan as compared to the preoperative CTA scan may be the result of an increase in neck length and/or diameter, both related to oversizing the stent graft in the aortic neck. Oversizing the neck diameter by 25%, for example, will result in coverage of the aortic wall below the >10% diameter increase that defines the distal end of the neck. Progressive changes in neck morphology may result in an increase or decrease in neck surface. Increased neck surface may be the result of progressive neck dilatation, possibly resulting in stent graft migration and type IA endoleak. Decrease in neck surface may indicate shortening of the neck as a result of the increasing aneurysm sac diameter.

For calculating the tubular member positional parameter, the patient model is, preferably automatically, analysed for predetermined parts of the stent for describing the position and apposition of the stent graft in the aortic neck in three dimensions.

It is for instance possible that a patient model obtained from the first postoperative computed tomography angiography (CTA) or similar scan, these parameters may determine the procedure success and the accuracy of the stent graft position, providing a baseline for further follow-up. During follow-up, subtle changes in these position characteristics or parameters indicate movement of the stent graft in the neck, which may predict late complications.

According to a preferred embodiment, the step of determining the tubular member positional parameter comprises identifying the proximal end of the stent graft in the patient model, preferably on the basis of proximally located markers, a proximal end of the stent frames on said stent graft and/or any predetermined landmarks of said stent graft. As mentioned above, it is then preferred if determining the apposition parameter comprises calculating a ratio or distance between the vessel morphology parameter, in particular as the proximal boundary of the vessel, and the tubular member positional parameter. A reliable parameter is thus obtained when the step of calculating the apposition parameter comprises calculating the shortest Euclidean distances in said patient model between the proximal end of the stent graft and branch arteries, for instance the renal arteries.

More specially, fabric distance is the straight-line distance between the stent graft fabric and branch arteries. From the patient model, for instance from the first postoperative CTA scan, the shortest fabric distance (SFD) determines the precision of the stent graft position and the longest fabric distance (LFD) indicates the potential neck on the contralateral side of the aorta that was not used for sealing. Increasing fabric distance during follow-up indicates migration of the stent graft.

As mentioned above, the angle between the center lumen line of the vessel and the centerline normal to said end surface of the tubular member is an reliable parameter for determining the position of the tubular member. For this particular case, the tilt is preferably determined as the angle between the stent graft fabric and the aortic centerline. Small degree of tilt indicates a position parallel to the aortic wall, while large degree of tilt requires more oversizing of the stent graft as compared to the neck diameter, in order to retain sufficient radial force onto the aortic wall. Change in tilt during follow-up indicates one-sided migration.

A change is diameter of the tubular member or graft expansion is further found to be a reliable parameter for determining the position of the tubular member. Therefore, the step of determining the tubular member positional parameter comprises determining a resting or initial diameter of the stent graft and determining from the patient model the diameter of the stent graft, wherein the apposition diameter is determined as a ratio between the two determined diameters. As mentioned above, the method may then not comprise the step of determining a vessel morphology parameter.

Graft expansion may be defined as the percentage of stent graft diameter that is expanded in the aortic neck as compared to the initial diameter of the stent graft's main body. When the stent graft is oversized 15-20% as compared to the aortic neck diameter (not accounting for mural neck thrombus), expansion would be expected to be 83-87%. Dilatation of the aortic neck would allow the graft to expand further, even reaching its original diameter (100% expansion).

Shortest apposition length is the shortest straight-line distance between the proximal circumference of the stent graft fabric and the first slice perpendicular to the CLL that shows interruption of full circumferential stent graft apposition. It defines the critical length of sealing at the site that is most at risk for a type IA endoleak. When the shortest apposition length approaches zero, apposition is lost and the risk for a type IA endoleak is eminent. Decreasing shortest apposition length during follow-up may be caused by stent graft migration or aneurysm sac expansion, shifting the distal boundary of the sealing in proximal direction.

As further mentioned above, the surface covered by the tubular member, also referred to as apposition surface (AS), wherein the apposition parameter is calculated as a ratio of the inner surface of the lumen of said vessel suitable for receiving the tubular member and the surface of the tubular member in contact with said inner surface of said lumen, is a reliable measure. Specifically, the apposition surface (AS) can be defined as the surface over which the stent graft fabric is in contact with the aortic wall. This surface has a proximal boundary, as previously defined, for instance through radiopaque markers located on the stent graft, indicating the proximal boundary of the graft fabric, and a distal boundary of the surface of the vessel as determined above, preferably as the first slice or section perpendicular to the center lumen line CLL that shows interruption of full circumferential stent graft apposition.

Also for this parameter, it is preferred if subsequent parameters determined from different patient models taking on different points of time are compared. Growth of the apposition surface during follow up is either caused by neck dilatation or prolongation of the sealing length, due to sac regression. Decreasing apposition surface may indicate stent graft migration or sac expansion, similar to the shortest apposition length. The apposition surface is preferably calculated from the first postoperative patient model, for instance CTA scans, and the percentage of neck surface (NS), covered by the stent graft is calculated ($AS_{post}/NS_{post}*100\%$).

The initial apposition surface, calculated from the first postoperative CTA scan, indicates the precision of the initial stent graft placement. Perfect placement, just below the origin of the branch artery to be preserved will result in 100% coverage of the neck. With decreasing percentages of coverage, the risk for proximal neck complications increases, especially in short necks. Reduced apposition surface during follow-up may be caused by either tilt or migration of the stent graft and increases the risk for type IA endoleak. In addition to the loss of apposition surface, tilt induces a second negative effect. With increasing tilt, the stent graft diameter that is needed for full circumferential apposition in the neck increases, due to the ellipsoid shape of the proximal graft end with large tilt. When the graft is heavily tilted, this may result in undersizing of the stent graft, despite sufficient initial oversizing (>10%), based on preoperative sizing perpendicular to the CLL. Sudden increase in apposition surface may be caused by an increase in neck length as a result of sac regression, which is a good sign, but also as a result of neck dilatation. The latter may be associated with graft migration and type IA endoleak, so would require careful follow-up. Especially when the expanded diameter reaches 100% of the initial diameter of the main body as mentioned above, the radial force is lost and migration becomes a serious threat. Our software clearly differentiates between beneficial or malicious increase in apposition surface.

The invention further relates to a method for determining a risk parameter indicating the risk of post-stent graft complications such as migration and/or type IA endoleak, comprising the steps of determining for at least two patient models as defined above the apposition parameters according to the invention, wherein the risk parameter is defined as at least one of:
  an increase (neck dilatation) or decrease (loss of apposition at distal apposition zone) of the Aortic Neck Surface ANS as defined above;
  an increase of the parameter based on branch artery distances, in particular shortest fabric distance (SFD) and longest fabric distance (LFD) as defined above;
  an increase of the parameter based on angle or tilt as defined above;
  an increase of the parameter based on the stent diameters, in particular graft expansion as defined above;
  a decrease of the parameter based on ratio of surfaces, in particular the apposition surface (AS) as defined above;

a decrease in the distance between the proximal end of the stent and the distal boundary of the neck, in particular defined as the shortest apposition length above.

It will be appreciated that the invention is not directly limited to the defining of an apposition parameter for a tubular member, or stent graft, for treating an infrarenal abdominal aortic aneurysm. The invention and parameters associated therewith are also applicable in defining stent placement for treating aneurysms in for instance the iliac artery, the brachial artery, the femoral artery or the renal artery. The invention may also be applied in other vessels or ducts than arteries, such as the ureter, the urethra, the oesophagus and the like.

The invention is further not limited to determining tubular member placement in relation to aneurysms. It is for instance possible that the method is used for determining the position and apposition of a tubular member, such as a stent, for treating occlusive diseases or treating other damage or leakage of a vessel or duct.

The invention is further not limited to a specific type of tubular member. The invention may be applied to tubular members such as stents, stent grafts or even shunts, which are to be placed in a vessel or duct in a patient.

The present invention is further illustrated by the following Figures and examples, which show a preferred embodiment of the device and method according to the invention, and are not intended to limit the scope of the invention in any way, wherein:

FIG. 1 schematically shows the method according to the invention.

FIGS. 2 and 3 show different parameters for determining the position and apposition of an stent graft in an aorta;

Figure 9:
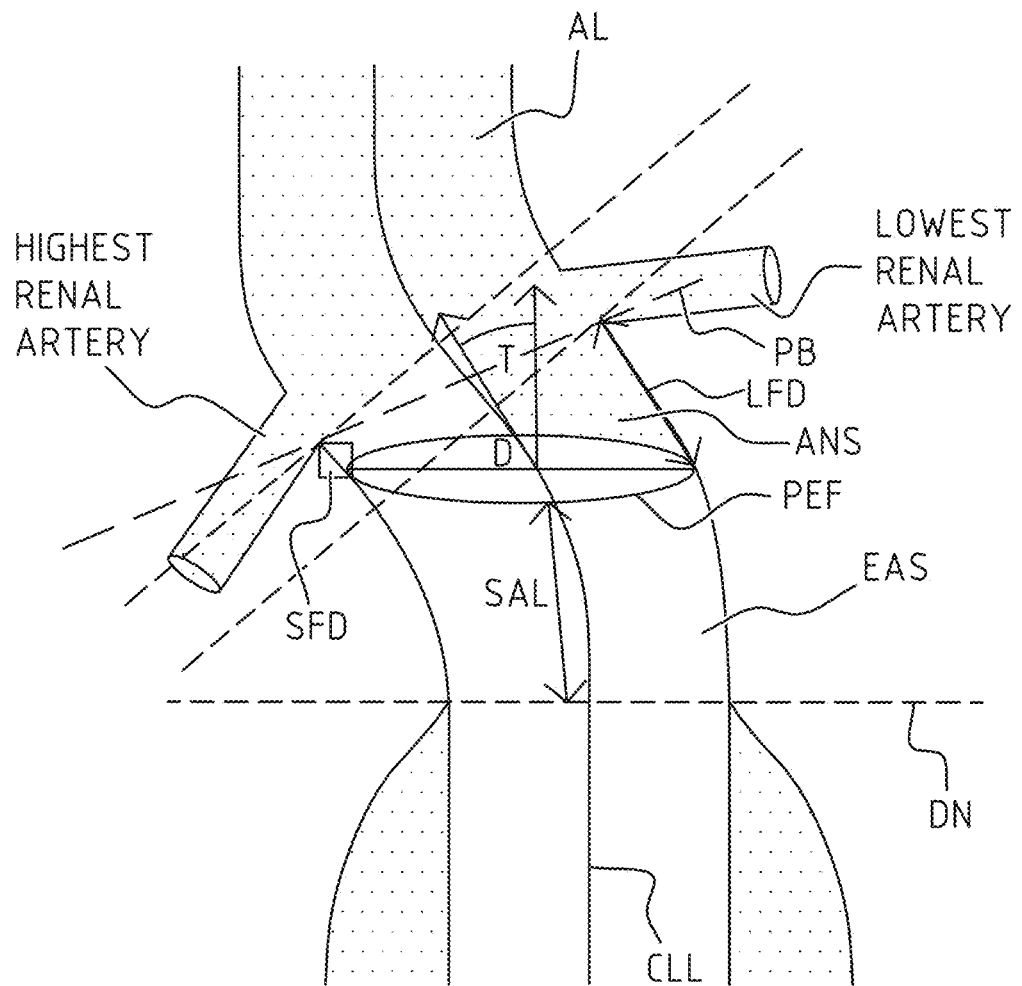

FIG. 9 schematically shows an overview of the parameters in relation to the aortic neck.

Figure 1:
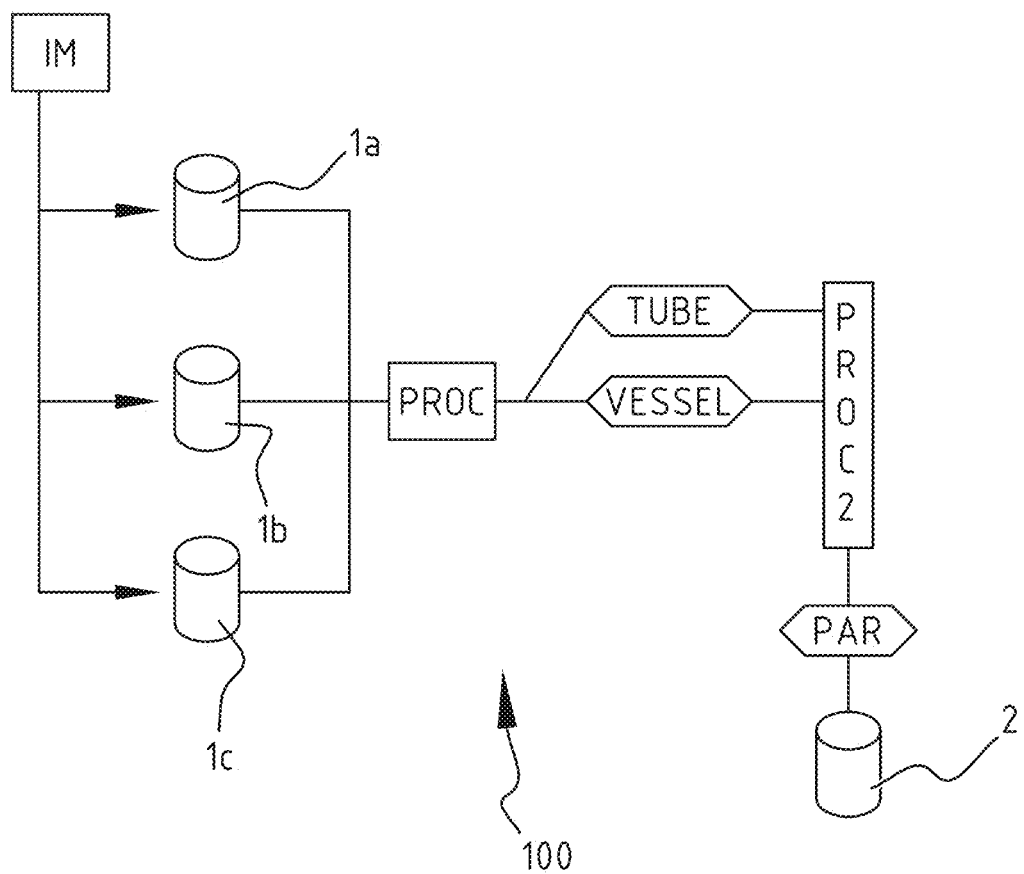

In FIG. 1, the method 100 according to the invention is schematically shown. The method according to the invention is preferably an automated, for instance computer implemented, method. The method can be performed by a standard computer, a dedicated processing unit or any suitable device.

The method is arranged to derive parameters from imaging data, which can for instance be imaging data obtained by an imaging device IM based on Computed Tomography (CT), Computed Tomography Angiography (CTA), Magnetic Resonance Imaging (MRI), Magnetic Resonance Angiography (MRA), and the like. From this imaging device, the imaging files may be stored and processed for obtaining digital patient models 1a-c which contain three-dimensional positional data of the morphology of the aorta and the stent inserted therein. In this example, dataset 1a contains preoperative data, such that this patient model does not contain information regarding the stent.

A processor PROC processes the patient models 1a-c and determines from the data parameters relating to the vessel morphology, indicated with VESSEL and/or parameters relating to the stent graft position, indicated with TUBE. As said, it may be possible that only vessel related parameters or only tube related parameters are calculated, for instance for comparison of these parameters between patient models 1a-c.

The parameters are processed by a second processor PROC2, which may be same processor as mentioned above, for determining a parameter PAR which is representative for the position and apposition of the stent graft in the aorta. This parameter, or the plurality of parameters, may be stored in a memory 2.

EXAMPLE

Five EVAR patients were retrospectively selected from St. Antonius Hospital's database. Four have been electively treated for an abdominal aortic aneurysm with occurrence of late (>1 year) type IA endoleak or significant endograft migration (>1 cm). A fifth patient without post-EVAR complications during follow-up was used as control. All patients underwent at least a pre-EVAR CT-scan and two post-EVAR CT-scans before the migration or type IA endoleak was determined. All CT-scans were part of regular EVAR follow-up and were assessed by radiologists according to a standardized protocol.

CT Scan Protocol

CT Angiography images were acquired on a 256 slices CT scanner. Scan parameters were: Tube voltage 120 kV, tube current time product 180 mAs preoperative and 200 mAs postoperative, distance between slices 0.75 mm, pitch 0.9 mm, collimation 128×0.625 mm preoperative, and 16 mm×0.75 mm postoperative. Preoperative slice thickness was 1.5, 3.2, 3.2, 2.0, and 3.0 mm for patients #1-#5 respectively. Postoperative slice thickness was 1.5 mm for all postoperative CT scans. Pre-EVAR, 100 ml Xenetix300 contrast was administered intravenously in the arterial phase with 4 ml per second. Post-EVAR, 80 ml was administered in the arterial phase with 3 ml per second.

Measurement Protocol

The aortic neck morphology was defined on the preoperative CT scan and every available post-operative CT scan of each patient. With use of the software implementing the method according to the invention, the position and apposition of the endograft within the aortic neck were determined for each patient at the post-operative CT scans.

Neck Morphology

The aortic neck characteristics included diameter, length and surface. The measurements were performed by an experienced observer on a 3Mensio vascular workstation V7.2 (Pie Medical, Maastricht, The Netherlands). A center lumen line (CLL) was drawn through the lumen of the aorta. The neck diameter was measured at the level of the distal boundary of the orifice of the lowest renal artery. The aortic neck length was measured as the distance over the CLL between the lowest renal artery and the distal end of the neck. On preoperative CT scans, the distal end of the neck was defined as a 10% increase in aortic diameter compared to the diameter at the level of the lowest renal artery. On postoperative CT scans, the distal end of the aortic neck was determined as the level where full circumferential apposition of the endograft with the aortic wall was lost. This is called the distal apposition boundary.

Dedicated software, developed in MATLAB 2015a (The MathWorks, Natick, Mass., USA), calculated the surface over a 3D mesh of the aortic lumen using the coordinates of the renal arteries and the coordinates of the distal end of the aortic neck. The mesh and coordinates were exported from 3Mensio.

The aortic neck surface (ANS) was calculated with this homemade software and defined as the neck surface that can be used for endograft apposition without overstenting one of the renal arteries R. The proximal boundary PB (FIG. 2A and FIG. 9) of the ANS was defined by the orifices of both renal arteries R. Pre-EVAR the ANS ends were the diameter of the neck is >10% of the diameter at the lowest renal artery R (the artery in the left of FIG. 2a), indicated with DN. Post-EVAR (FIG. 2B), the ANS ends when the full circumferential endograft apposition with the aortic wall is lost, also indicated with DN in FIG. 2B. The aortic neck surface was calculated over the aortic segment that was located between these boundaries PB, DN.

Endograft Position

The endograft position was defined by the terms fabric distances, tilt and endograft expansion. These characteristics were calculated with the software on the basis of the proximal end of the endograft fabric (PEF), see FIGS. 3A and 9. The PEF was defined by identification of the 3D coordinates of the endograft fabric markers measured in 3Mensio. With use of the software the PEF can be projected on the mesh of the aortic lumen AL.

The fabric distances are the Euclidean straight-line distances from the PEF to the coordinates of both renal arteries R (FIG. 3A). The shortest fabric distance (SFD) and longest fabric distance (LFD) are independent of which renal artery R is the highest on CLL measurements. Increase in either SFD or LFD during follow-up will be indicative for endograft migration.

Tilt T of the endograft in the aorta was defined as the angle between the centerline CLL of the aortic neck and the centerline CL of the PEF (FIGS. 3B and 9). Endograft expansion is calculated as the average diameter of the PEF of the endograft (3D intersection with the aortic neck) and measured as absolute value as well as percentage of the original maximum possible endograft diameter. Endograft expansion may be the result of neck dilatation, endograft tilt and migration. The relationship between endograft expansion and oversizing is shown in Table 1.

TABLE 1

Relationship between endograft oversizing and endograft expansion. This relationship is independent of the endograft diameter.

| | Oversizing of endograft [%] | | | |
|---|---|---|---|---|
| | 10 | 15 | 20 | 25 |
| Endograft expansion [% of original endograft diameter] | 91 | 87 | 83 | 80 |

The method allows determination of all parameters at the first post-EVAR CT scan as baseline and eventual changes during follow-up.

Endograft Apposition

The endograft apposition surface (EAS) is defined as the surface of the aortic neck where the endograft seals the aortic wall. This parameter can be calculated as absolute value as well as percentage of the maximum aortic neck surface (ANS) that could be sealed. The EAS was calculated as the surface over the mesh of the aortic lumen between the PEF and the distal apposition boundary (FIG. 1C). A decrease of EAS may be an early indicator of endograft migration or neck dilatation.

Figure 3C:
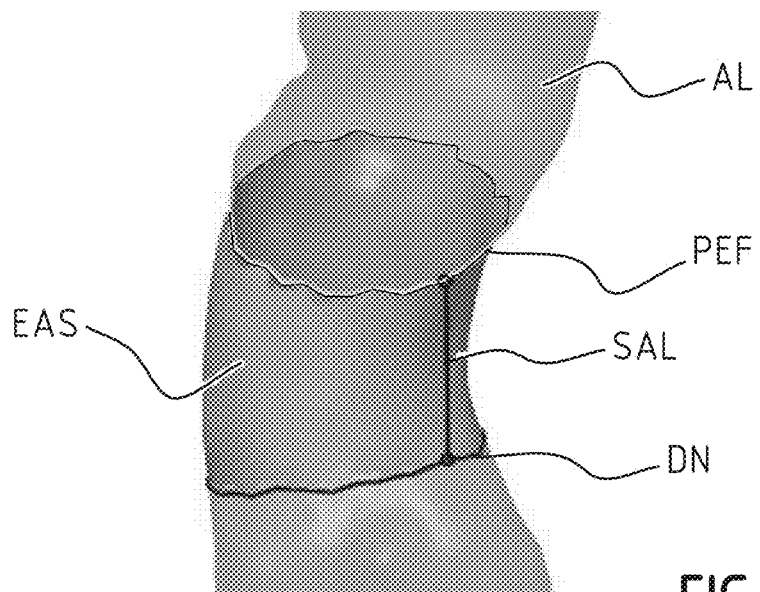

Because of the 3D intersection of the endograft with the aortic wall the lowest point of the endograft fabric will not always be straight below the renal arteries. Therefore, we defined the shortest apposition length (SAL) which is the shortest distance between the endograft fabric PEF and the distal apposition boundary DN somewhere at the 3D intersection between endograft and aortic wall (FIGS. 3c and 9).

Warning Signs

Initial suboptimal endograft placement, observed on the first postoperative CT scan, and change in position and apposition during follow-up may forecast the onset of post-EVAR complications. On the basis of the new measuring software six parameters can describe aortic neck morphology and the initial position and apposition of the endograft in the aortic neck, as listed in table 2 below:

TABLE 2

Baseline parameters at first postoperative CT scan

Aortic neck surface (ANS)
Fabric distances (SFD, LFD)
Tilt of the endograft
Endograft expansion (% of the original endograft diameter)
Endograft apposition surface (EAS, % of ANS)
Shortest apposition length These parameters at the first postoperative CT scan are used as baseline for follow-up. During follow-up, subtle changes in ANS, endograft position, and EAS may occur before type IA endoleak of substantial migration are obvious. In table 3, 7 warning signs that indicate change in endograft position during follow-up are described.

TABLE 3

Warning signs that indicate change in endograft position during follow-up, potentially predicting migration and type IA endoleak.

Increase of ANS (neck dilatation)
Decrease of ANS (loss of apposition at distal apposition zone)
Increase of fabric distance (SFD, LFD)
Increase of endograft tilt
Increase of endograft expansion (% of the original endograft diameter)
Decrease of EAS (% of ANS)
Decrease of shortest apposition length These warning signs were analysed on the CT scans of five patients, in order to illustrate the added value over regular (and current standard) follow-up.

Patient Examples

Five EVAR patients were selected, one without late aortic neck associated complications (patient #1), and four diagnosed with endograft migration or type IA endoleak after >1 year follow-up. Two patients suffered from type IA endoleak (patients #2 and #3, diagnosed 493 and 1273 days after the primary procedure, respectively). Two patients were diagnosed with significant (>1 cm) migration (patients #4 and #5, diagnosed 1197 and 1659 days after the primary EVAR procedure, respectively).

Patient #1

Figures 4A, 4B, 4C:
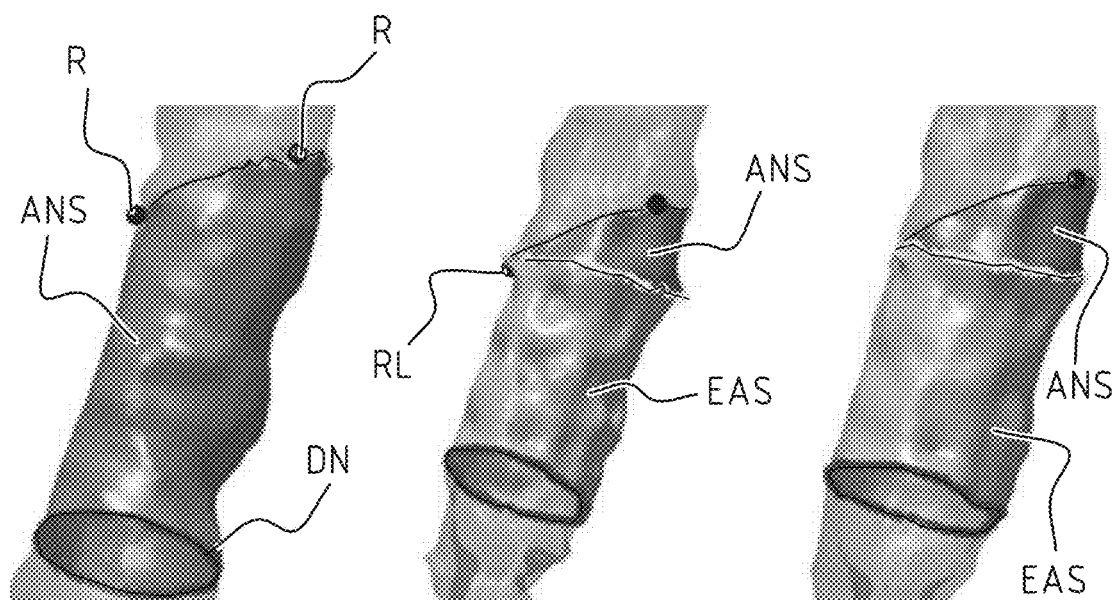
FIGS. 4-8 show stent graft position and apposition of different patients.

FIGS. 4A-C and Table 4 show a case of stable endograft position and EAS without early or late neck associated complications one year post-EVAR.

FIG. 4A shows the pre-EVAR aortic neck surface (ANS) between the renal arteries R and the distal end of the neck DN. FIG. 4B shows that the endograft EAS is well positioned just at the level of the lowest renal artery RL 41 days post-EVAR. According to FIG. 4C there are no warning signs in position and apposition of the endograft compared with the first follow-up CT scan at 393 days post-EVAR (besides slight increase in tilt).

No warning signs were detected at the last follow-up CT scan compared to the first follow-up CT scan (Table 4). Endograft expansion increased slightly, but the endograft was still 19% oversized at one year follow-up.

TABLE 4

Neck characteristics and endograft position and apposition for patient #1.

|  | Pre-EVAR 48 days | Post-EVAR 41 days | Post-EVAR 393 days |
|---|---|---|---|
| Neck diameter (mm) | 24 | 24 | 25 |
| Original endograft diameter (mm) [type] | 28 [Endurant[a]] | | |
| Neck length (mm) | 43 | | |
| SFD (mm) | | 0 | 0 |
| LFD (mm) | | 11 | 12 |
| Tilt (°) | | 3 | 8 |
| Endograft expansion [mm, and % original endograft diameter] | | 23 [80%] | 24 [84%] |
| Shortest apposition length (mm) | | 28 | 28 |
| ANS (mm², and % of the first post-EVAR CT scan) | | 2704 (100%) | 2907 [108%] |
| EAS (mm², and % of the ANS) | | 2330 [86%] | 2544 [88%] |

[a]Medtronic, Minneapolis, Minn., USA
SFD = Shortest Fabric Distance
LFD = Longest Fabric Distance
ANS = Aortic Neck Surface
EAS = Endograft Apposition Surface

TABLE 5

Neck characteristics and endograft position and apposition for patient #2.

|  | Pre EVAR 21 days | Post-EVAR 59 days | Post-EVAR 493 days |
|---|---|---|---|
| Neck diameter (mm) | 23 | 25 | 23 |
| Original endograft diameter (mm) [type] | 26 [Talent[a]] | | |
| Neck length (mm) | 11 | | |
| SFD (mm) | | 10[b] | 13[b] |
| LFD (mm) | | 15 | 17 |
| Tilt (°) | | 3 | 2 |
| Endograft expansion [mm, and % original endograft diameter] | | 26 [98%][b] | 26 [100%][b] |
| Shortest apposition length (mm) | | 3[b] | 0[b] |
| ANS (mm², and % of the first post-EVAR CT scan) | | 1465 | 1298 [89%] |
| EAS (mm², and % of the ANS) | | 355 [24%][b] | 45 [3%][b] |

[a]Medtronic, Minneapolis, Minn., USA
[b]Warning signs
SFD = Shortest Fabric Distance
LFD = Longest Fabric Distance
ANS = Aortic Neck Surface
EAS = Endograft Apposition Surface Patient #2

Figure 5A:
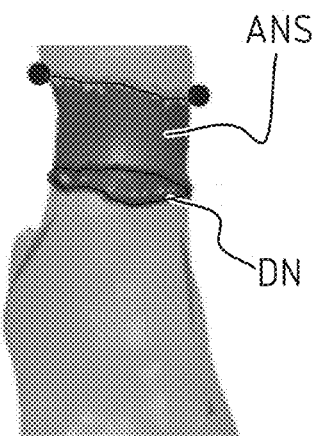
Figure 5B:
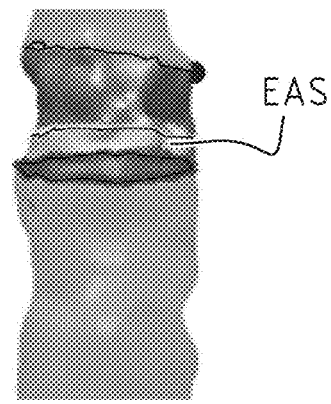
Figure 5C:
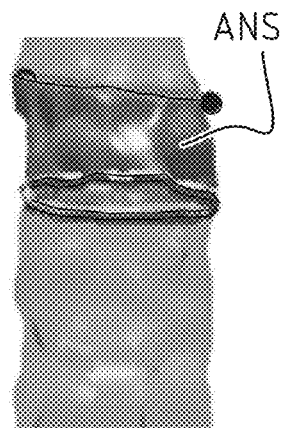

FIGS. 5A-C and Table 5 show the results of a patient were the endograft position at the first post-EVAR CT scan was insufficient, and four warning signs were observed (FIG. 5B); 1. Fabric distance to the lowest renal artery is 10 mm, 2. shortest apposition length is only 3 mm, 3. endograft expansion is 98% of the original diameter (only 2% oversizing), and 4. the EAS is only 24% of the ANS (see FIG. 5A). The completion angiography during the EVAR procedure showed that the endograft was positioned 1-2 mm below the lowest renal artery, so the endograft must have been migrated between the primary implant and the first post-EVAR CT scan. The radiologist scored the position of the endograft on this first follow-up CT scan as "uneventful" with adequate sealing and no evidence for endoleaks. On the second follow-up CT scan all warning signs remained present and a type IA endoleak and a complete loss of endograft apposition were visible (FIG. 5C).

Patient #3

Figure 6A:
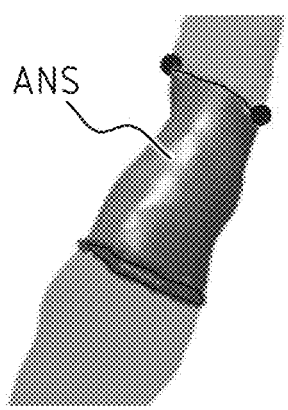
Figure 6B:
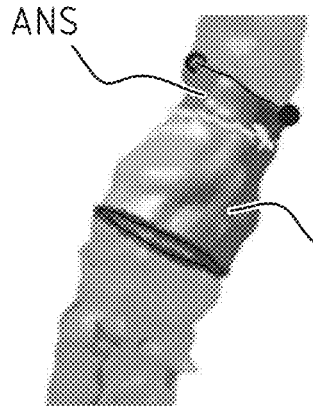
Figure 6C:
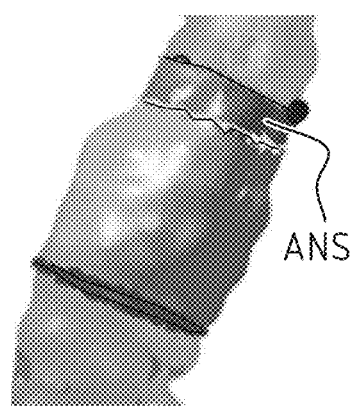
Figure 6D:
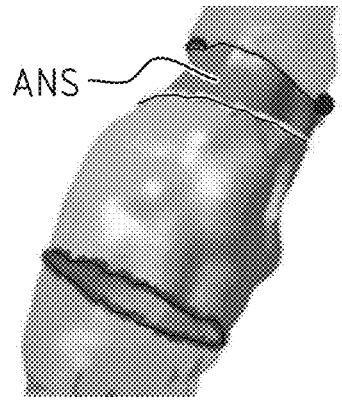
Figure 6E:
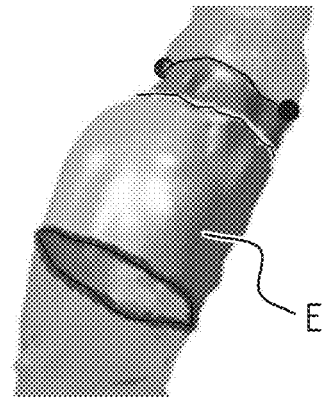
Figure 6F:
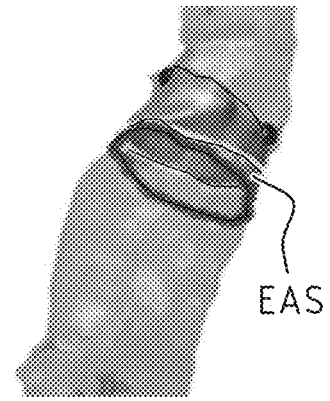

FIGS. 6A-F and Table 6 show a patient diagnosed with a type IA endoleak 1273 days post-EVAR. The preoperative neck is of sufficient length, indicated with ANS in FIG. 6A and not angulated. A large endograft apposition surface (EAS) is visible 38 days post-EVAR. On the 251 days post-EVAR CT scan, two important warning signs are present (FIG. 6B): 1. Substantial increase of the ANS as a result of neck dilatation that is not observed at baseline level, 2. Expansion of the endograft diameter (change from 33% initial oversizing to 15% oversizing at 251 days follow-up). FIGS. 6C-E show a progressive dilatation of the aortic neck occurs during 251-911 days follow-up, without migration of the endograft. On the 911 days post-EVAR CT scan (FIG. 6E), the endograft oversizing was reduced to 9%. The radiologist reported no dilatation of the aortic neck, but only an increase of the aneurysm diameter without signs of an endoleak. A type IA endoleak was observed on the CT scan 1273 days post-EVAR (FIG. 6F).

TABLE VI

Aortic neck characteristics and endograft position and apposition for patient #3.

|  | Pre-EVAR 28 days | Post-EVAR 61 days | Post-EVAR 251 days | Post-EVAR 541 days | Post-EVAR 911 days | Post-EVAR 1273 days |
|---|---|---|---|---|---|---|
| Neck diameter (mm) | 21 | 21 | 21 | 21 | 22 | 22 |
| Original endograft diameter (mm) [type] | 28 [Endurant[a]] | | | | | |
| Neck length (mm) | 14 | | | | | |
| SFD (mm) | | 6 | 6 | 6 | 6 | 6 |
| LFD (mm) | | 9 | 7 | 9 | 7 | 13[b] |
| Tilt (°) | | 17 | 18 | 13 | 16 | 15 |
| Endograft expansion [mm, and % original endograft diameter] | | 21 [75%] | 24 [87%][b] | 24 [87%][b] | 26 [92%][b] | 27 [95%][b] |
| Shortest apposition length (mm) | | 22 | 29 | 28 | 28 | 0[b] |
| ANS (mm², and % of the first post-EVAR CT scan) | | 2578 | 3444 [134%][b] | 3638 [141%][b] | 3594 [139%][b] | 1026 [40%][b] |

TABLE VI-continued

Aortic neck characteristics and endograft position and apposition for patient #3.

|  | Pre-EVAR 28 days | Post-EVAR 61 days | Post-EVAR 251 days | Post-EVAR 541 days | Post-EVAR 911 days | Post-EVAR 1273 days |
|---|---|---|---|---|---|---|
| EAS [mm$^2$, and % of the ANS) |  | 2051 [80%] | 2855 [83%] | 3006 [83%] | 2955 [82%] | 231 [23%][b] |

[a]Medtronic, Minneapolis, Minn., USA
[b]Warning signs
SFD = Shortest Fabric Distance
LFD = Longest Fabric Distance
ANS = Aortic Neck Surface
EAS = Endograft Apposition Surface Patient #4

Figure 7A:
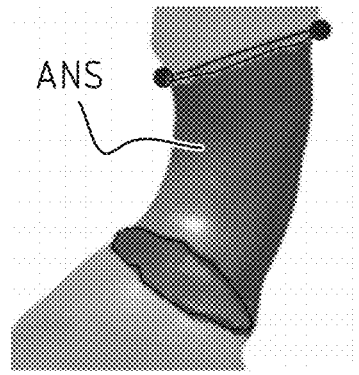
Figure 7B:
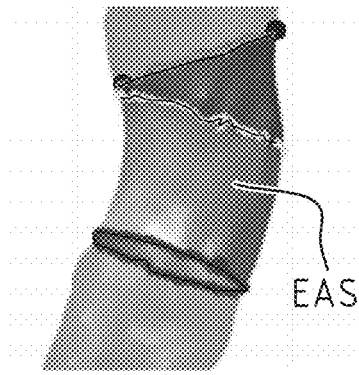
Figure 7C:
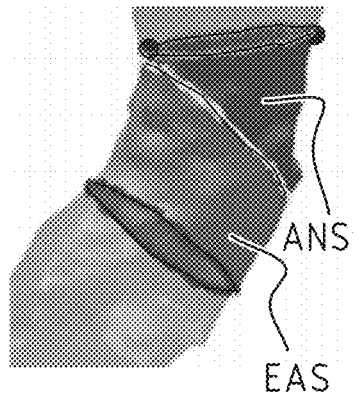

FIGS. 7A-C and table 7 show a patient with increasing tilt of the endograft during follow-up. No warning signs were present on the CT scan 32 days post-EVAR, with the exception of substantial tilt (FIG. 7B). On the second post-EVAR CT scan (FIG. 7C), multiple warning signs were present: 1. An increase in tilt (from 20.0° to 28.5°), which results into 2. Increased endograft expansion of 99% of the initial diameter (only 1% oversizing left), and 3. Decrease in EAS. No endoleak was reported after 1659 days follow-up. Four months later, a type IA endoleak was diagnosed with duplex ultrasound.

TABLE 7

Aortic neck characteristics and endograft position and apposition for patient #4.

|  | Pre-EVAR 57 days | Post-EVAR 32 days | Post-EVAR 1659 days |
|---|---|---|---|
| Neck diameter (mm) | 27 | 27 | 28 |
| Original endograft diameter (mm) [type] | 29 [Excluder[a]] |  |  |
| Neck length (mm) | 33 |  |  |
| SFD (mm) |  | 2 | 4 |
| LFD (mm) |  | 19 | 24[b] |
| Tilt (°) |  | 20[b] | 29[b] |
| Endograft expansion [mm, and % original endograft diameter] |  | 25 [87%] | 28 [99%][b] |
| Shortest apposition length (mm) |  | 20 | 15[b] |
| ANS (mm$^2$, and % of the first post-EVAR CT scan) |  | 2425 | 2680 [110%] |
| EAS [mm$^2$, and % of the ANS) |  | 1658 [68%] | 1492 [56%][b] |

[a]W. L. Gore & Associates, Inc., Flagstaff, Arizona, USA.
[b]Warning signs
SFD = Shortest Fabric Distance
LFD = Longest Fabric Distance
ANS = Aortic Neck Surface
EAS = Endograft Apposition Surface Patient #5

Figure 8A:
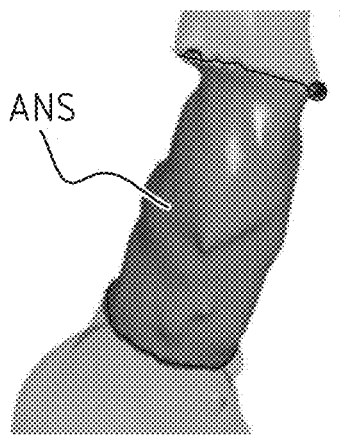
Figure 8B:
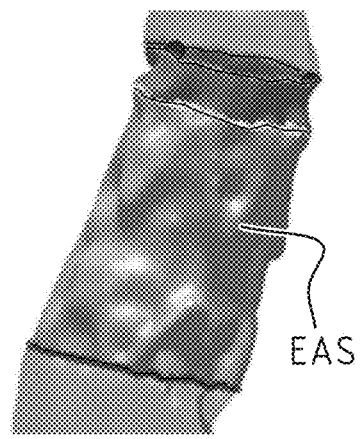
Figure 8C:
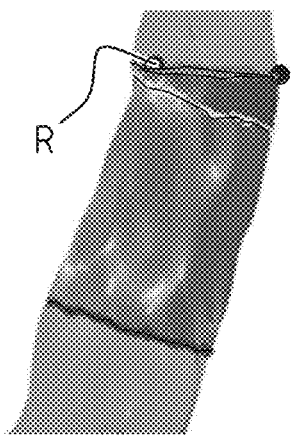
Figure 8D:
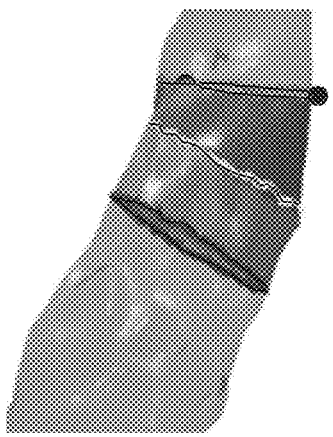
Figure 8E:

FIGS. 8A-E and table 8 show a case of endograft migration, tilt, and aortic neck dilatation. FIG. 8a shows the pre-EVAR neck surface ANS. According to FIG. 8B, a good endograft apposition surface EAS is achieved 86 days post-EVAR. On the 369 days follow-up CT scan (FIG. 8C), three warning signs were observed: 1. Increased tilt of the endograft, 2. Migration of 3 mm at the level of the lowest renal artery RL, and 3. Increased expansion of the endograft. After 890 days (FIG. 8D), almost all warning signs were present. The aortic neck was dilated, leading to further expansion of the endograft and decreased sealing at the distal part of the neck. The endograft had been migrated and EAS was obviously decreased. In the radiology only endograft migration was determined at the 890 days post-EVAR CT-scan and no reintervention was performed. On the 1197 days CT scan (FIG. 8E), complete loss of apposition and subsequent type IA endoleak was observed.

The present invention is not limited to the embodiment shown, but extends also to other embodiments falling within the scope of the appended claims.

The invention claimed is:

1. A method for determining an apposition parameter which is indicative for the position and apposition of a tubular member inserted in a lumen of an anatomical vessel or duct of a patient, the method comprising the steps of:
  providing a numerical three-dimensional patient model of at least a part of the vessel of the patient including the tubular member, wherein the three-dimensional patient model comprises three-dimensional positional data of the morphology of the vessel and positional data of the tubular member in said vessel;
  determining at least one vessel morphology parameter from the patient model, which parameter is indicative for the anatomy of a predetermined part of the vessel at or near the tubular member in said vessel with respect to said patient model;
  determining at least one tubular member positional parameter from the patient model, which parameter is indicative for the position of a predetermined part of the tubular member in the patient model; and
  calculating, on the basis of the determined vessel morphology parameter and tubular member positional parameter, the relative position of the tubular member with respect to the vessel as the apposition parameter,
wherein: the steps of:
  determining the vessel morphology parameter comprises determining at least one of the proximal and distal boundary in said vessel suitable for receiving the tubular member;
  determining the tubular member positional parameter comprises determining the position of the proximal, respectively distal end of the tubular member in said vessel, and;
  calculating the apposition parameter comprises calculating a ratio between the at least one of the proximal and distal boundary in said vessel and the position of the proximal, respectively distal end of the tubular member;

or the steps of:
- determining the vessel morphology parameter comprises determining a center lumen line extending to the cross sectional centers of the lumen along a predetermined length of the vessel;
- determining the tubular member positional parameter comprises determining at least one of a proximal and distal end of the tubular member in said vessel and determining the centerline normal to said end surface; and
- calculating the apposition parameter comprises calculating the angle between the center lumen line and the centerline normal to said end surface;

or the steps of:
- determining the vessel morphology parameter comprises determining an inner surface of the lumen of said vessel suitable for receiving the tubular member;
- determining the tubular member positional parameter comprises determining the surface of the tubular member in contact with said inner surface of said lumen; and
- calculating the apposition parameter comprises calculating a ratio between the inner surface of the lumen and the surface of the tubular member in contact with said inner surface.

2. The method according to claim 1, wherein the step of determining the vessel morphology parameter comprises determining at least one of the diameter, length and surface of the vessel suitable for receiving said tubular member.

3. The method according to claim 1, wherein the vessel morphology parameter and the tubular member positional parameter define the anatomy, respectively position in the same three-dimensional coordinate system of the patient model.

4. The method according to claim 1, wherein the step of determining the proximal and/or distal boundary in said vessel comprises identifying in said patient model branch vessels of said vessel.

5. The method according to claim 1, wherein the step of determining at least one of the proximal and distal boundary in said vessel comprises identifying the boundary of the aneurysm by identifying a predetermined increase in vessel diameter in said patient model.

6. The method according to claim 1, comprising:
- providing a first numerical three-dimensional patient model obtained from a patient at a first point of time and determining at least one of the parameters from said first patient model;
- providing a second numerical three-dimensional patient model obtained from said patient at a second point of time different from said first point of time and determining at least one of the parameters from said second patient model; and
- calculating the apposition parameter on the basis of the parameters determined from the two numerical three-dimensional patient models.

7. The method according to claim 6, further comprising the step of providing a numerical three-dimensional pre-operative patient model of at least a part of the vessel of the patient not including the tubular member obtained prior to insertion of the tubular member and calculating at least one of the parameters from said pre-operative patient model.

8. The method according to claim 1, wherein the step of providing a numerical three-dimensional patient model comprises obtaining a three-dimensional image data from a medical imaging technique, such as Computed Tomography (CT), Computed Tomography Angiography (CTA), Magnetic Resonance Imaging (MRI), Magnetic Resonance Angiography (MRA), and the like, and processing said image data for obtaining said numerical three-dimensional patient model.

9. The method for determining an apposition parameter which is indicative for the position and apposition of a stent graft in the thoracoabdominal aorta and/or at least one iliac artery of a patient after endovascular aneurysm repair according to claim 1.

10. The method according to claim 9, wherein the step of determining the vessel morphology parameter comprises determining at least one of the diameter, length and surface of the aortic neck in said patient model.

11. The method according to claim 10, wherein the length and surface of the aortic neck are determined on the basis of the determined proximal and distal boundaries of the aortic neck, wherein the length is determined along the center lumen line, extending to the cross sectional centres of the lumen along a predetermined length of the vessel.

12. The method according to claim 9, wherein the step of determining the vessel morphology parameter comprises identifying the positions in the patient model of at least one branch artery and determining the proximal boundary in said vessel suitable for receiving the tubular member as the position in the patient model on the basis of the positions of the branch artery.

13. The method according to claim 12, wherein the step of calculating the apposition parameter comprises calculating the shortest Euclidean distances in said patient model between the proximal end of the stent graft and branch arteries.

14. The method according to claim 9, wherein the step of determining the vessel morphology parameter comprises determining the distal boundary of the aortic neck, wherein determining the distal boundary comprises at least one of:
- in the patient model, determining the first slice perpendicular to the center lumen line of the aortic neck that shows interruption of full circumferential stent graft apposition; and
- in a pre-operative patient model of at least a part of the vessel of the patient not including the tubular member obtained prior to insertion of the tubular member and calculating at least one of the parameters from said pre-operative patient model, determining the first slice to exceed a 10% increase of the average aortic diameter at baseline.

15. The method according to claim 9, wherein the step of determining the tubular member positional parameter comprises identifying the proximal end of the stent graft in the patient model on the basis of proximal located markers and/or a proximal end of the stent frames on said stent graft.

16. The method according to claim 9, wherein determining the tubular member positional parameter comprises determining a resting or initial diameter of the stent graft and determining from the patient model the diameter of the stent graft, wherein the apposition diameter is determined as a ratio between the two determined diameters.

17. A method for determining an apposition parameter which is indicative for the position and apposition of a stent graft inserted in a lumen of an anatomical vessel or duct of a patient, the method comprising the steps of:
- providing a numerical three-dimensional patient model of at least a part of the vessel of the patient including the stent graft, wherein the three-dimensional patient model comprises three-dimensional positional data of the morphology of the vessel and positional data of the stent graft in said vessel;

determining at least one vessel morphology parameter from the patient model, which parameter is indicative for the anatomy of a predetermined part of the vessel at or near the stent graft in said vessel with respect to said patient model;

determining at least one stent graft positional parameter from the patient model, which parameter is indicative for the position of a predetermined part of the stent graft in the patient model; and calculating, on the basis of the determined vessel morphology parameter and stent graft positional parameter, the relative position of the stent graft with respect to the vessel as the apposition parameter.

18. The method according to claim 17, comprising:

providing a first numerical three-dimensional patient model obtained from a patient at a first point of time and determining at least one of the parameters from said first patient model;

providing a second numerical three-dimensional patient model obtained from said patient at a second point of time different from said first point of time and determining at least one of the parameters from said second patient model; and calculating the apposition parameter on the basis of the parameters determined from the two numerical three-dimensional patient models.

19. The method for determining an apposition parameter which is indicative for the position and apposition of a stent graft in the thoracoabdominal aorta and/or at least one iliac artery of a patient after endovascular aneurysm repair according to claim 17.

20. A method for determining a risk parameter indicating the risk of post-stent graft complication, comprising the steps of:

determining, for at least a first numerical three-dimensional patient model obtained from a patient at a first point in time and a second numerical three-dimensional patient model obtained from said patient at a second point of time different from said first point of time, apposition parameters indicative for the position and apposition of a tubular member inserted in a lumen of an anatomical vessel or duct of a patient, wherein the risk parameter is defined as at least one of:

an increase or decrease of the surface of the aortic neck in said patient models; an increase of the parameter based on the shortest Euclidean distances in said patient models between a proximal end of the tubular member and a branch artery;

an increase of the parameter based on an angle between a center lumen line extending to a cross-sectional center of the lumen along a predetermined length of the vessel and a centerline normal to the surface of at least one of a proximal and a distal end of the tubular member in said vessel;

an increase of the parameter based on a resting or initial diameter of the tubular member and the diameter of the tubular member determined from the patient model;

a decrease of the parameter based on an inner surface of the lumen of said vessel suitable for receiving the tubular member and the surface of the tubular member in contact with said inner surface of said lumen; and a decrease in the distance between the proximal end of the tubular member and the distal boundary of the neck.

* * * * *